US006596692B1

United States Patent
Burman et al.

(10) Patent No.: US 6,596,692 B1
(45) Date of Patent: Jul. 22, 2003

(54) SUBSTANCE P ANALOGS FOR THE TREATMENT OF CANCER

(75) Inventors: Anand C. Burman, Ghaziabad (IN); Sudhanand Prasad, Ghaziabad (IN); Rama Mukherjee, Ghaziabad (IN); Manu Jaggi, Ghaziabad (IN); Anu T. Singh, Ghaziabad (IN)

(73) Assignee: Dabur Research Foundation, Ghaziabad (IN)

( * ) Notice: Subject to any disclaimer, the term of this patent is extended or adjusted under 35 U.S.C. 154(b) by 0 days.

(21) Appl. No.: 09/629,642

(22) Filed: Jul. 31, 2000

(51) Int. Cl.$^7$ .................. A61K 38/00; A61K 38/04; C07K 16/00
(52) U.S. Cl. ................. 514/14; 514/15; 514/16; 530/327; 530/328; 530/329
(58) Field of Search ................. 514/14, 15, 16; 530/328, 327, 329

(56) References Cited

U.S. PATENT DOCUMENTS

| 5,410,019 A | 4/1995 | Coy et al. ............ 530/323 |
| 5,434,132 A | 7/1995 | Rozengurt et al. ......... 514/2 |

FOREIGN PATENT DOCUMENTS

| EP | 0835562 | 4/1998 |
| WO | 8909232 | 10/1985 |

OTHER PUBLICATIONS

Jaine, Sci. Amer., vol. 271, pp. 58–65, Jul. 1994.*
Curti, Critical Reviews in Oncology/Hematology, vol. 14, pp. 29–39, 1993.*
Ross et al., Immunology Today, vol. 11, No. 6, 1990.*
Siemen, in Rodent Tumor Model in Experimental Cancer Therapy, edited by Robert F. Kallman, published by Pergamon Press, 1987, pp. 12–15.*
Trott, in Rodent Tumor Models in Exaperimental Cancer Therapy, edited by Robert F. Kallman, published by Pergamon Press, 1987, pp. 6–11.*
Chemical Abstract No. 130:333171 Iwamura, Masatugu et al. Suprusion of the Urol. Oncol.4(1). (1999), Volume Date 1998, pp24–28.
Jarpe, M.B. et al. [$_D$–Arg$^1$ , $_D$–Phe$^5$ , $_D$–Trp$^7$, $^9$, Leu$^{11}$] Substance P Acts as a Biased Agonist Toward Neuropeptide and Chemokine Receptors*. Journey of Biological Chemistry, vol.273,No. 5, (1998) pp 3097–3104.
Secki, M.J. et al."[$_D$–Arg$^1$ , $_D$–Trp$^5$, $^7$, $^9$, Leu$^{11}$]Substance P: A Novel Potent Inhibitor of Signal Transduction and Growth in Vitro and in Vivo in Small Cell Lung." Cancer Research, 57(1) (1997) pp 51–54.
Frucht, et al.; Cancer Research 52 : 1114–1122, Mar. 1, 1992.

* cited by examiner

Primary Examiner—Christopher S. F. Low
Assistant Examiner—Abdel A. Mohamed
(74) Attorney, Agent, or Firm—Ladas & Parry (57) ABSTRACT

The present invention encompasses novel synthetic peptide analogs that are antagonists to Substance P, substance P like peptides and related peptides and are useful for the treatment of cancer. The invention particularly relates to the design and synthesis of the novel substance P antagonist analogs incorporating α,α-dialkylated amino acids in a site specific manner. The invention encompasses methods for the generation of these peptides, compositions containing these peptides and pharmacological applications of these peptides specifically in the treatment and prevention of cancer.

22 Claims, 1 Drawing Sheet

Figure 1

SUBSTANCE P ANALOGS FOR THE TREATMENT OF CANCER

FIELD OF INVENTION

The present invention encompasses novel synthetic peptide analogs that are antagonists to Substance P, substance P like peptides and related peptides and are useful for the treatment of cancer. The invention particularly relates to the design and synthesis of the novel substance P antagonist analogs incorporating α,α-dialkylated amino acids in a site specific manner. The invention encompasses methods for the generation of these peptides, compositions containing these peptides and pharmacological applications of these peptides specifically in the treatment and prevention of cancer.

BACKGROUND OF THE INVENTION

Substance P is one of the main members of the tachykinin family. The tachykinins are mammalian regulatory peptides and are present in the central and peripheral nervous systems, and in gut endocrine cells. Substance P was the first gut neuropeptide to be discovered. It is a 11 residue neuropeptide of the following sequence:

Arg-Pro-Lys-Pro-Gln-Gln-Phe-Phe-Gly-Leu-Met-NH$_2$ (SEQ ID NO: 1)

Substance P regulates gastrointestinal motility, increases blood flow in the gut, stimulates secretion of the pancreas, salivary glands, small intestines and inhibits acid secretion. In the central nervous system, tachykinins play a role in the sensory nervous pathways and in motor control. (Dockray, G. J., 1994, 401 Gut peptides: Biochemistry and Physiology, Raven Press Ltd, New York).

The role of Substance P in cancer has been well recognized particularly in small cell lung cancer. Small cell lung cancer (SCLC) cell growth is sustained by multiple autocrine and paracrine growth loops involving neuropeptides. In the search for novel antiproliferative agents for small cell lung cancer the first substance P antagonist to be studied was [D-Arg$^1$, D-Pro$^2$, D-Trp$^{7,9}$, Leu$^{11}$] substance P (Antagonist A). Substance P is structurally unrelated to bombesin/GRP and has no bombesin/GRP antagonist activity; antagonist A was found to block the secretory effects of bombesin on a pancreatic preparation, diminish bombesin/GRP binding to its receptor and inhibit mitogenesis in Swiss 3T3 cells (Jensen et al., 1984, Nature, 309; 61–63; Zachary and Rozengurt, 1986, Biochem. Biophys. Res. Commun., 137;135–141). However it did not affect mitogenesis induced by polypeptide growth factors, such as platelet-derived growth factor and epidermal growth factor. Among other congeners of substance P tested for bombesin/GRP antagonism, two compounds with inhibitory activity were identified: antagonist D, [D-Arg$^1$, D-Phe$^5$, D-Trp$^{7,9}$, Leu$^{11}$] substance P, and antagonist G [Arg$^6$,D-Trp$^{7,9}$, MePhe$^8$] substance P(6–11). Antagonist D was shown to be five fold more potent than antagonist A in preventing the cellular effects of bombesin/GRP and vasopressin in mouse 3T3 cells and in inhibiting the growth of SCLC cells in serumfree medium. Overall, in Swiss 3T3 cells both antagonists were demonstrated to have in common the ability not only to inhibit the effects of bombesin/GRP but also the effects of other neuro-peptides, including vasopressin, bradykinin, endothelin, and substance P. This is also reflected by data showing that antagonist G is ten fold less potent than antagonist D in blocking bombesin/GRP mediated mitogenesis in Swiss 3T3 cells and it is almost as potent as antagonist D in inhibiting SCLC proliferation in vitro. Antagonist D inhibited proliferation of H-510 and H-69 SCLC cells in liquid culture and in semi-solid media (IC50=5 μM). Colony formation stimulated by multiple neuropeptides including vasopressin and bradykinin was also blocked by Antagonist D (Seckl, M. J. et al.,1997, Can Res, 57(1):51–4). In addition, antagonist G showed inhibition of SCLC xenografts in vivo (Wolf P. J. and Rozengurt, E., 1990, Can. Res., 50(13):3968–73; Everard, M. J., et al., 1993, Eur J Cancer, 29A(10):1450–3; Br J Cancer, 1992, 65(3):388–92)). Reeve, J. G. and Bleehen, N. M. (Biochem. Biophys. Res. Commun.,1994, 199(3):1313–19) found that treatment of lung tumor cells with Antagonist D caused a concentration-dependent loss of cell viability which was accompanied by the onset of apoptosis as defined by cytological criteria and DNA fragmentation.

Short-chain SP antagonist viz.pHOPA-D-Trp-Phe-D-Trp-Leu-Leu-NH2 (Analog R) (SEQ ID NO: 2) and its analogs were studied by the Hungarian group and were found to inhibit the proliferation of H69 SCLC cells both in vitro and in xenografts in vivo in nude mice (Int. J. Cancer, 1995,60 (1):82–7). In a further extension of the work, the C-terminal peptide bond was replaced by a methylene-amino (pseudopeptide) bond. Substance P analogues: D-MePhe-D-Trp-Phe-D-TrpLeu(psi)-(CH$_2$NH)-Leu-NH$_2$) (SEQ ID NO: 3); Analog 6 and D-MePhe-D-Trp-Phe-DTrp-Leu-MPA (SEQ ID NO: 4): Analog 7, inhibited SCLC pro-liferation more effectively than Analog R (6: IC50=2 μM; 7: IC50=5 μM and R: IC50=10 μM). Moreover, Analog 6 inhibited the respiratory activity of SK-MES 1 epithelial type of lung carcinoma cells in proliferating but not in the quiescent state suggesting that the anti-proliferative effect of these compounds is not due to simple cytotoxicity and these short chain SP analogues may be promising candidates as therapeutic agents in the treatment of SCLC (Nyeki, O. ,et.al., 1998, J. Pept. Sci, 4(8): 486–95). Antagonist D and its role in cancer has been described in the U.S. Pat. No. 5,434,132 and WO 88/07551.

The present invention describes peptide analogs of substance P, the preparation, and use of peptide analogs of substance P especially the Antagonist D of substance P using constrained amino acids and their use thereof for cancer therapy, alone, or in combination or as an adjunct to cancer chemotherapy.

The design of conformationally constrained bioactive peptide derivatives has been one of the widely used approaches for the development of peptide-based therapeutic agents. Non-standard amino acids with strong conformational preferences may be used to direct the course of polypeptide chain folding, by imposing local stereochemical constraints, in de novo approaches to peptide design. The conformational characteristics of α,α-dialkylated amino acids have been well studied. The incorporation of these amino acids restricts the rotation of φ,Ψ angles within the molecule, thereby stabilizing a desired peptide conformation. The prototypic member of α,α-dialkylated aminoacids, α-amino-isobutyric acid (Aib) or (α,α-dimethyl glycine has been shown to induce (3-turn or helical conformation when incorporated in a peptide sequence (Prasad and Balaram, 1984, CRC Crit. Rev. Biochem.16, 307–347; Karle and Balaram, 1990 Biochemistry, 29, 6747–6756). The conformational properties of the higher homologs of α,α-dialkylated amino acids such as diethylglycine (Deg), di-n-propylglycine (Dpg) and di-n-butylglycine (Dbg) as well as the cyclic side chain analogs of a,a-dialkylated amino acids such as 1-aminocyclopentane carboxylic acid (Ac5c), 1-amino-cyclohexane carboxylic acid (Ac6c), as 1-aminocycloheptane carboxylic acid. (Ac7c) and as 1-aminocyclooctane carboxylic acid (Ac8c) have also been shown to induce folded conformation (Prasad, S. et al., 1995 Bioploymers, 35, 11–20; Karle, L. L.,et al., 1995, J. Amer. Chem. Soc.,117, 9632–9637). α,α-Dialkylated amino acids have been used in the design of highly potent chemotactic peptide analogs (Prasad, S. et al., 1996 Int. J. Peptide Protein Res. 48, 312–318.) However, the applicants are not aware of any prior art for the synthesis of novel peptide analogs, encompassed in the present invention, particularly the synthesis of such substance P peptide analogs, containing α,α-dialkylated amino acids. Moreover, the use of such constrained amino acids for the design of peptides possessing anti-neoplastic activity is also unknown in any previous prior art. The present invention exploits the conformational properties of such α,α-dialkylated amino acids for the design of biologically active peptide derivatives of substance P with specific anticancer activity. Furthermore in the prior art it has been shown that lipophilazation of bioactive peptides improves the stability, bioavailability and ability to permeate biomembranes (Dasgupta, P et al; 1999, Pharmaceutical Res. 16, 1047–1053; Gozes, I. et al., 1996, Proc. Natl. Acad. Sci. USA, 93, 427–432).

The present invention also includes synthesized peptide derivatives having N-terminal alkanoyl groups from 2–18 carbon atoms with improved anticancer activity.

Abbreviations and Symbols

In the formula (I) below and throughout the specification and claims the amino acids residues are designated by their standard abbreviations. Amino acids denote L-configuration unless otherwise indicated by D or DL appearing before the symbol and separated from it by hyphen.

The following abbreviations are also used in this application:

| | |
|---|---|
| Aib = | α-Aminoisobutyric acid |
| Deg = | α,α-Di-ethylglycine |
| Dpg = | α,α-Di-n-propylglycine |
| Ac5c = | 1-Aminocyclopentanecarboxylic acid |
| Ac6c = | 1-Aminocyclohexane carboxylic acid |
| BOP: | Benzotriazole-1-yl-oxy-tris-(dimethylamino)-phosphonium hexofluorophosphate |
| PyBOP: | Benzotriazole-1-yl-oxy-tris-pyrrolidino-phosphonium hexofluorophospate |
| HBTU: | O-Benzotriazole-N,N,N',N'-tetramethyl-uronium-hexofluoro-phosphate |
| TBTU: | 2-(1H-Benzotriazole-1yl)-1,1,3,3-tetramethyluronium tetrafluoroborate |
| HOBt: | 1-Hydroxy Benzotriazole |
| DCC: | Dicyclohexyl carbodiimide |
| DICPDI: | Diisopropyl carbodiimide |
| DIEA: | Diisopropyl ethylamine |
| DMF: | Dimethyl formamide |
| DCM: | Dichloromethane |
| NMP: | N-Methyl-2-pyrrolidinone |
| TFA: | trifluoroacetic acid |

SUMMARY OF INVENTION

The present invention comprises polypeptides of the following general formula:

X-D-Arg-Pro-Lys-Pro-D-Phe-Gln-D-Trp-Phe-D-Trp-Leu-R-NH$_2$ wherein,
X is acetyl or straight, branched, or cyclic alkanoyl group from 3 to 18 carbon atoms, or is deleted;
R is Aib, Deg, Dpg, AcSc or Ac6c; or R is a hydrolyzable carboxy protecting group; or a pharmaceutically acceptable salt of the peptide.

DETAILED DESCRIPTION OF THE INVENTION

The novel peptide analogs of substance P embodied in the present invention contain amino acids, namely α,α-dialkylated amino acids, which have been known to induce highly specific constraints in the peptide backbone. The (α,α-dialkylated amino acids, used in the present invention are synthesized from the corresponding ketones. In a preferred embodiment of the invention, the ketones are first converted into the corresponding hydantoins which are hydrolyzed to yield the aforesaid amino acids. In a preferred embodiment of the present invention, sulphuric acid, hydrochloric acid or a strong base such as NaOH has been employed as the hydrolyzing agent.

The present invention comprises polypeptides of the following general formula:

X-D-Arg-Pro-Lys-Pro-D-Phe-Gln-D-Trp-Phe-D-Trp-Leu-R-NH$_2$ wherein,
X is acetyl or straight, branched, or cyclic alkanoyl group from 3 to 18 carbon atoms, or is deleted;
R is Aib, Deg, Dpg, AcSc or Ac6c; or R is a hydrolyzable carboxy protecting group; or a pharmaceutically acceptable salt of the peptide.

A hydrolyzable carboxy protecting group are those groups which on hydrolysis converts to carboxylic group such as —CONH2, —COOMe, etc.

Preferably the alkyl portion of the alkanoyl group is from 2 to 12 carbon atoms. Preferred alkanoyl groups are acetyl, butanoyl, octanoyl, lauroyl, myristoyl, palmitoyl, n-hexanoyl, isohexanoyl, cyclohexanoyl, cyclopentylcarbonyl, heptanoyl, decanoyl, n-undecanoyl, and 3,7-dimethyloctanoyl.

Salts encompassed within the term "pharmaceutically acceptable salts" refer to non-toxic salts of the compounds of this invention. Representative salts and esters include the following:

acetate, ascorbate, benzenesulfonate, benzoate, bicarbonate, bisulfate, bitartrate, borate, camsylate, carbonate, citrate, dihydrochloride, methanesulfonate, ethanesulfonate, p-toluenesulfonate, cyclohexylsulfamate, quinate, edetate, edisylate, estolate, esylate, fuxnarate, gluconate, glutamate, glycerophophates, hydrobromide, hydrochloride, hydroxynaphthoate, lactate, lactobionate, laurate, malate, maleate, mandelate, mesylate, mucate, napsylate, nitrate, n-methylglucamine, oleate, oxalate, palmoates, pamoate (embonate), palmitate, pantothenate, perchlorates, phosphate/diphosphate, polygalacturonate, salicylates, stearate, succinates, sulfate, sulfamate, subacetate, succinate, tannate, tartrate, tosylate, trifluoroacetate, and valerate.

Other salts include Ca, Li, Mg, Na, and K salts; salts of amino acids such as lysine or arginine; guanidine, diethanolamine or choline; ammonium, substituted ammonium salts or aluminum salts.

The salts are prepared by conventional methods.

The present invention also encompasses fragments of the above peptides having the formula:

D-Phe-Gln-D-Trp-Phe-D-Trp-Leu-R- NH$_2$ wherein,

R is Aib, Deg, Dpg, Ac5c or Ac6c; or

R is a hydrolyzable carboxy protecting group; or a pharmaceutically acceptable salt of the peptide.

The carboxy protecting group and salts are as defined above.

The preferred novel analogs of substance P of the present invention are as follows:

D-Arg-Pro-Lys-Pro-D-Phe-Gln-D-Trp-Phe-D-Trp-Leu-Ac5c-$NH_2$ (SEQ ID NO: 5)

Acetyl-D-Arg-Pro-Lys-Pro-D-Phe-Gln-D-Trp-Phe-D-Trp-Leu-Ac5c-$NH_2$ (SEQ ID NO: 6)

Butanoyl-D-Arg-Pro-Lys-Pro-D-Phe-Gln-D-Trp-Phe-D-Trp-Leu-Ac5c-$NH_2$ (SEQ ID NO: 7)

Octanoyl-D-Arg-Pro-Lys-Pro-D-Phe-Gln-D-Trp-Phe-D-Trp-Leu-Ac5c-$NH_2$ (SEQ ID NO: 8)

Lauroyl-D-Arg-Pro-Lys-Pro-D-Phe-Gln-D-Trp-Phe-D-Trp-Leu-Ac5c-$NH_2$ (SEQ ID NO: 9)

D-Arg-Pro-Lys-Pro-D-Phe-Gln-D-Trp-Phe-D-Trp-Leu-Ac6c-$NH_2$ (SEQ ID NO: 10)

Butanoyl-D-Arg-Pro-Lys-Pro-D-Phe-Gln-D-Trp-Phe-D-Trp-Leu-Ac6c-$NH_2$ (SEQ ID NO: 11)

Octanoyl-D-Arg-Pro-Lys-Pro-D-Phe-Gln-D-Trp-Phe-D-Trp-Leu-Ac6c-$NH_2$ (SEQ ID NO: 12)

D-Arg-Pro-Lys-Pro-D-Phe-Gln-D-Trp-Phe-D-Trp-Leu-Aib-$NE_2$ (SEQ ID NO: 13)

D-Arg-Pro-Lys-Pro-D-Phe-Gln-D-Trp-Phe-D-Trp-Leu-Deg-$NH_2$ (SEQ ID NO: 14)

D-Arg-Pro-Lys-Pro-D-Phe-Gln-D-Trp-Phe-D-Trp-Leu-Dpg-$NH_2$ (SEQ ID NO: 15)

D-Phe-Gln-D-Trp-Phe-D-Trp-Leu-Aib-$NH_2$ (SEQ ID NO: 16)

D-Phe-Gln-D-Trp-Phe-D-Trp-Leu-Ac5c-$NH_2$ (SEQ ID NO: 17)

D-Phe-Gln-D-Trp-Phe-D-Trp-Leu-Ac6c-$NH_2$ (SEQ ID NO: 18)

D-Phe-Gln-D-Trp-Phe-D-Trp-Leu-Deg-$NH_2$ (SEQ ID NO: 19)

D-Phe-Gln-D-Trp-Phe-D-Trp-Leu-Dpg-$NH_2$ (SEQ ID NO: 20)

Pharmaceutical compositions suitable for use in present invention include compositions wherein the active ingredients are contained in an effective amount to achieve its intended purpose.

The term "an effective amount" means that amount of a drug or pharmaceutical agent that will elicit the biological or medical response of a tissue, system, animal or human that is being sought. In addition to the active ingredients, these pharmaceutical compositions may contain suitable pharmaceutically acceptable earners excipients, diluents, solvents, flavoring, colorants etc. The preparations may be formulated in any form including but not limited to tablets, dragees, capsules, powders, syrups, suspensions, slurries, time released formulations, sustained release formulations, pills, granules, emulsions, patches, injections, solutions, liposomes and nanoparticles.

Suitable routes for administration are those known in the art and include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

The exact formulation, route of administration and dosage can be chosen by the individual physician in view of the patient's condition.

Toxicity and therapeutic efficacy of the peptides of this invention can be determined by standard pharmaceutical procedures in cell cultures or experimental animals.

SYNTHESIS OF PEPTIDES

The novel peptides in the present invention have been generated by using solid phase techniques, by a combination of solution phase procedures and solid phase techniques or by fragment condensation. These methods for the chemical synthesis of polypeptides are well known in the art (Stewart and Young, 1969, Solid Phase Peptide Synthesis, W.H. Freeman Co.).

In a preferred embodiment of the present invention the peptides were synthesized using the Fmoc strategy, on a semi automatic peptide synthesizer (CS Bio, Model 536), using optimum side chain protection. The peptides were assembled from C-terminus to N-terminus. Peptides amidated at the carboxy-terminus were synthesized using the Rink Amide resin. The loading of the first Fmoc protected amino acid was achieved via an amide bond formation with the solid support, mediated by Diisopropylcarbodiimide (DIPCDI) and HOBt. Substitution levels for automated synthesis were preferably between 0.2 and 0.8 mmol amino acid per gram resin.

The N-terminal amino group was protected by 9-fluorenyl-methoxycarbonyl (Fmoc) group. Trityl (trt) or t-butyloxycarbonyl (Boc) were the preferred protecting groups for imadazole group of Histidine residue. The hydroxyl groups of Serine, Threonine and Tyrosine were preferably protected by t-butyl group (tBu) 2,2,5,7,8-pentamethyl-chroman-6-sulfonyl (Pmc) or 2,2,4,7,-pentamethyl-dihydrobenzenofuran-5-sulfonyl (Pbf) were the preferred protecting groups for the guandino group of Arginine. Trityl was the preferred protecting group for Asparagine and Glutamine and tertiary butyl group (tBu) was the preferred protecting group for Aspartic acid and Glutamic acid. The tryptophan residue was either left unprotected or used with Boc protection. The side chain amino group of Lysine was protected using Boc group preferably.

In a preferred embodiment of the invention, 2–8 equivalents of Fmoc protected amino acid per resin nitrogen equivalent were used. The activating reagents used for coupling amino acids to the resin, in solid phase peptide synthesis, are well known in the art. These include DCC, DIPCDI, DIEA, BOP, PyBOP, HBTU, TBTU, and HOBt. Preferably, DCC or DIPCDI/HOBt or HBTU/HOBT and DIEA were used as activating reagents in the coupling reactions.

The protected amino acids were either activated in situ or added in the form of preactivated esters known in the art such as NHS esters, Opfp esters etc. Atherton, E. etal, 1988, J. Chem. Soc., Perkin Trans. I, 2887. Bodansky, M. in "The Peptides, Analysis, Synthesis and Biology" (E. Gross, J, Meienhofer, eds) Vol. 1, Academic Press, New York, 1979, 106.

The coupling reaction was carried out in DMF, DCM or NMP or a mixture of these solvents and was monitored by Kaiser test (Kaiser et al., Anal. Biochem., 34, 595–598 (1970)). In case of a positive Kaiser test, the appropriate amino acid was recoupled using freshly prepared activated reagents.

After the assembly of the peptide was completed, the amino-terminal Fmoc group was removed and then the peptide-resin was washed with methanol and dried. The peptides were then deprotected and cleaved from the resin support by treatment with trifluoroacetic acid, crystalline phenol, ethanedithiol, thioanisole and de-ionized water for 1.5 to 5 hours at room temperature. The crude peptide was obtained by precipitation with cold dry ether, filtered, dissolved, and lyophilized.

The resulting crude peptide was purified by preparative high performance liquid chromatography (HPLC) using a LICHROCART® $C_{18}$ (250. Times. 10) (reverse phase C-18 column) reverse phase column (Merck, Darmstadt, Germany) on a Preparative HPLC system (Shimadzu Corporation, Japan) using a gradient of 0.1% TFA in acetonitrile and water. The eluted fractions were reanalyzed on Analytical HPLC system (Shimadzu Corporation, Japan) using a C18 LICHROSPHERG®, WP-300 (300×4) (reverse phase C18 column) reverse-phase column. Acetonitrile was evaporated and the fractions were lyophilized to obtain the pure peptide. The identity of each peptide was confirmed by electron-spray mass spectroscopy.

Preferred, semi-automated, stepwise solid phase methods for synthesis of peptides of the invention are provided in the examples discussed in the subsequent section of this document.

The present invention will be further described in detail with reference to the following examples, as will be appreciated by a person skilled in the art is merely illustrative and should not be construed as limiting. Various other modifications of the invention will be possible without departing from the spirit and scope of the present invention.

The steps involved in the synthesis of the Substance P analogs employed the following protocol:

TABLE I

| STEP | REAGENT | MIX TIME (MIN) | NO. OF CYCLES |
|---|---|---|---|
| 1. | Methylene chloride | 1 | 2 |
| 2. | Dimethyl formamide | 1 | 1 |
| 3. | 20% Piperidine in Dimethyl formamide | 1 | 1 |
| 4. | 20% Piperidine in Dimethyl formamide | 29 | 1 |
| 5. | Dimethyl formamide | 1 | 3 |
| 6. | Isopropanol | 1 | 2 |
| 7. | Methylene chloride | 1 | 2 |
| 8. | Amino Acid | Variable | 1 |
| 9. | Dimethyl formamide | 1 | 2 |
| 10. | Stop or Return for next cycle | | |

EXAMPLE 1

First Loading on Rink Amide Resin

A typical preparation of the Fmoc-AcSc-Rink Amide Resin was carried out using 1.0 g of 4-(2',4'-Dimethoxyphenyl-Fmoc-aminomethyl) phenoxymethyl-derivatized polystyrene 1% divinylbenzene (Rink Amide) resin (0.7 mM/g) (100–200 mesh), procured from Advanced Chemtech, Louisville, Ky. U.S.A. Swelling of the resin was typically carried out in dichloromethane measuring to volumes 10–40 ml/g resin. The resin was allowed to swell in methylene chloride (2×25 ml, for 10 min.). It was washed once in dimethylformamide (DMF) for 1 min. All solvents in the protocol were added in 20 ml portions per cycle. The Fmoc-protecting group on the resin was removed by following steps 3–7 in the protocol. The deprotection of the Fmoc group was checked by the presence of blue beads in Kaiser test. For loading of the first amino acid on the free amino ($NH_2$) group of the resin, the first amino acid, was weighed in three to six fold excess, along with a similar fold excess of HOBt, in the amino acid vessel of the peptide synthesizer. These were dissolved in dimethylformamide (A.C.S. grade) (J. T. Baker, New Jersey, U.S.A.) and activated with DIPCDI, just prior to the addition to the resin in the reaction vessel of the peptide synthesizer. HOBt was added in all coupling reactions, especially in the case of glutamine and histidine. The coupling reaction was carried out for a period ranging from 1–3 hours. The loading of the amino acid on the resin was confirmed by the presence of colorless beads in the Kaiser Test. The loading efficiency was ascertained by the increase of weight of the resin after the addition of the amino acid.

EXAMPLE 2

Synthesis of D-Phe-Gln-D-Trp-Phe-D-Trp-Leu-AcSc-NH$_2$ (SEO ID NO: 17)

The synthesis of peptide SEQ ID NO:17 was initiated by using resin loaded with Fmoc-Ac5c-OH as prepared in Example 1 above on 1 g scale. This was subjected to stepwise deprotection and coupling steps as in steps 1–10 of the synthesis cycle. In each coupling reaction, a four-fold excess of amino-acid, DICPDI and HOBt were used. On completion of synthesis and removal of the N-terminal Fmoc protecting group (steps 1–6 of the synthesis cycle), the peptide-resin was washed twice with methanol, dried and weighed to obtain 1.649 g. This was subjected to cleavage in a cleavage mixture consisting of trifluoroacetic acid and scavengers, crystalline phenol, thioanisole, ethanedithol and water for a period of 1–4 hours at room temperature with continuous stirring. The peptide was precipitated using cold dry ether to obtain the crude peptide. The crude peptide was purified on a C18 preparative reverse phase HPLC column (250×10) on a gradient system comprising acetonitrile and water in 0.1% TFA as described previously in the art. The prominent peaks were collected and lyophilized, reanalysed on analytical HPLC and subjected to mass spectrometry. There was a good agreement between the observed molecular weight and calculated molecular weight (Calculated mass 1036; Observed Mass=1037.2 ). The pure peptide was then used for bioassays.

EXAMPLE 3

Synthesis of D-Arg-Pro-Lys-Pro-D-Phe-Gln-D-Trp-Phe-D-Trp-Leu-Ac5c-NH$_2$ (SEO ID NO: 5)

The synthesis was carried out as in the examples above using the appropriate amino acids. It was further cleaved and purified as described in Example 2. The purified peptide was further characterized by its mass analysis. The calculated mass of the above peptide was ~1515 and the observed mass was 1514.29.

EXAMPLE 4

Synthesis of Butanoyl-D-Arg-Pro-Lys-Pro-D-Phe-Gln-D-Trp-Phe-D-Trp-Leu-Ac5cNH$_2$ (SEQ ID NO:7)

The conjugation of the Butanoyl group at the N-terminal position was done on solid phase.

The above peptide sequence was synthesized on resin as described in Example 2. After the deprotection of D-Arg amino acid it was further coupled with Butanoic acid in DMF using DIPCDI and HOBT following the standard protocol. The cleavage and purification was further carried out following the standard protocol as described in Example 2. The final purified peptide was further analyzed by mass spectroscopy. The calculated mass and observed was in good agreement. (calculated mass is about ~1585, observed mass=1586).

EXAMPLE 5

Synthesis of Octanoyl-D-Arg-Pro-Lys-Pro-D-Phe-Gln-D-Trp-Phe-D-Trp-Leu-Ac5cNH$_2$ (SEQ ID NO:8)

The conjugation of the octanoyl group at the N-terminal position was done on solid phase.

The above peptide sequence was synthesized on resin in a similar way as described in Example 4 except octanoic acid is used in place of butanoic acid. The final purified peptide was further analyzed by mass spectroscopy. The calculated mass and observed was in good agreement. (calculated mass is about ~1641, observed mass=1642.2).

EXAMPLE 6

Synthesis of Acetyl-D-Arg-Pro-Lys-Pro-D-Phe-Gln-D-Trp-Phe-D-Try-Leu-Ac5c-NH$_2$ (SEQ ID NO:6)

The conjugation of the Acetyl group at the N-terminal position was done on solid phase using acetic anhydride in a similar way as described in Example 4. The final purified peptide was further analyzed by mass spectroscopy. The calculated mass and observed was in good agreement. (calculated mass is about ~1557, observed mass=1558.5).

EXAMPLE 7

In vitro Cytotoxic Activity of the Novel Synthesized Peptide Analogs

The cytotoxic activity of synthesized peptides was tested on six human tumor cell lines namely MCF7 (breast), U373 (glioblastoma), PTC, (colon), L132 (lung), Su.86.86 (pancreas), and KB (oral). The tumor cells were collected at exponential growth phase and resuspended in medium (1.5× 10$^6$ cells/ml in RPMI 1640 containing 10% FBS). 150 µL of medium was added to the wells of a 96-well tissue culture plate (Nunc, Denmark) followed by 30 µl of cell suspension. The plate was left in an incubator (37° C., 5% CO$_2$) overnight. 20 µl of the peptide (100 pM to 10 µM concentration) was added to marked wells of the 96-well plate. Each concentration was plated in triplicate. 20 µl of medium alone was added to control wells while wells without cells served as blanks. A total volume of 200 µL was ensured in each well and plate was left in incubator (37° C., 5% CO$_2$). After 72 hours of incubation an MTT assay was performed and percentage cytotoxicity was calculated with respect to control cells. Tables 2 and 3 show the cytotoxicity achieved in various cancer cell lines of different peptides.

CYTOTOXIC ACTIVITY OF (SEQ ID NO: 7)

TABLE 2

| Cell Line | Percentage cytotoxicity at different concentrations | | | | | |
|---|---|---|---|---|---|---|
| | 10 µM | 1 µM | 100 nM | 10 nM | 1 nM | 100 pM |
| MCF-7 | 19.7 ± 5 | 11.7 ± 5.1 | 15.4 ± 0.7 | 5.7 ± 1.5 | 20.55 ± 3.1 | 19.3 ± 1.8 |
| U373 | 21.1 ± 1.7 | 8.3 ± 0.5 | 8.8 ± 0.2 | 6.6 ± 0.7 | 13.4 ± 4.6 | 10.9 ± 1.0 |
| PTC | 27.3 ± 5.4 | 11.7 ± 3.0 | 5.3 ± 0.2 | 5.8 ± 0.2 | Nil | Nil |
| L132 | 15 ± 2.3 | 9 ± 2.3 | 9 ± 2.3 | 19 ± 3.3 | 25 ± 8 | 14 ± 3.4 |
| Su8686 | 38 ± 4.3 | 36 ± 3.3 | 15 ± 3.8 | 10 ± 2.8 | 25 ± 5.3 | 6 ± 1.8 |
| KB | 15 ± 2.3 | 4 ± 2.6 | 10 ± 4.9 | 10 ± 3.4 | 6 ± 0.9 | Nil |

CYTOTOXIC ACTIVITY OF (SEQ ID NO: 5)

TABLE 3

| Cell Line | Percentage cytotoxicity at different concentrations | | | | | |
|---|---|---|---|---|---|---|
| | 10 µM | 1 µM | 100 nM | 10 nM | 1 nM | 100 pM |
| MCF-7 | 18.4 ± 6.4 | 12.4 ± 2.6 | 8.6 ± 1.6 | 7.5 ± 1.5 | 2.4 ± 1.2 | Nil |
| U373 | 37.2 ± 5.3 | 17.06 ± 1.9 | 4.5 ± 0.5 | 5.0 ± 0.7 | 3.1 ± 0.5 | 3.7 ± 0.5 |
| PTC | 35.5 ± 4.8 | 25.5 ± 4.8 | 6.7 ± 1.3 | 3.1 ± 1.9 | 3.1 ± 0.5 | Nil |
| L132 | 23 ± 2.3 | 20 ± 2.3 | 21 ± 1.2 | 19 ± 3.3 | 15 ± 5.8 | 18 ± 3.4 |
| Su8686 | 25 ± 4.3 | 22 ± 3.3 | 9 ± 3.8 | 12 ± 2.8 | 3 ± 0.3 | Nil |

EXAMPLE 8

In vitro Cytotoxic Activity of Lipo Conjugates of Substance P Analogs

The cytotoxic effect of lipo-conjugates of substance P analogs SEQ ID NO: 6, SEQ ID NO: 7 and SEQ ID NO: 8, was studied by MTT assay which is based on the principle of uptake of MTT [3-[4,5-dimethylthiazol-2-yl]-2,5-diphenyl tetrazolium bromide], a tetrazolium salt by the metabolically active cells where it is metabolized by active mitochondria in to a blue colored formazan product which can be read spectrophotometrically. Briefly, tumor cells—KB (Oral squamous), U87MG (glioblastoma), HBL100 (Breast), HeP2 (Laryngeal), ECV304 (Endothelial), PA-1 (Ovary) and L132 (Lung) were incubated with the peptide analogs for 48 hours at 37° C. in a 96-well culture plate, followed by the addition of 100 µg MTT and further incubation of 1 hour. The formazan crystals formed inside the cells were dissolved with a detergent comprising of 100% Sodium dodecyl sulfate and 0.01 N HCl and optical density read on a multiscan ELISA reader. The optical density was directly proportional to the number of proliferating and metabolically active cells. Percent cytotoxicity of peptide analogs is shown in the following Table.

SEQ ID NO: 6

Percentage cytotoxicity at different concentrations

| Cell Lines | 1 µM | 100 nM | 10 nM | 1 nM |
|---|---|---|---|---|
| KB | 2.0 ± 1.3 | 18.0 ± 2.6 | 29.0 ± 1.3 | 28.0 ± 2.3 |
| U87MG | 31.8 ± 3.2 | 34.7 ± 1.9 | 32.9 ± 2.4 | 26.9 ± 3.5 |
| HBL100 | 28.9 ± 1.44.8 | 31.8 ± 1.5 | 28.4 ± 1.8 | 28.5 ± 4.5 |
| HeP2 | 13.8 ± 2.4 | 24.9 ± 1.5 | 14.8 ± 4.4 | 10.0 ± 3.2 |
| L132 | 19.7 ± 2.5 | 19.5 ± 4.6 | 24.7 ± 3.2 | 14.9 ± 2.9 |
| PA-1 | 13.9 ± 3.3 | 25.4 ± 2.6 | 22.0 ± 3.4 | 8.0 ± 24 |
| ECV304 | 12.9 ± 2.2 | 15.9 ± 2.3 | 13.8 ± 3.3 | 9.0 ± 3.7 |

SEQ ID NO: 7

Percentage cytotoxicity at different concentrations

| Cell Lines | 1 µM | 100 nM | 10 nM | 1 nM |
|---|---|---|---|---|
| KB | 9.0 ± 5.3 | 18.0 ± 5.2 | 21.9 ± 4.1 | 20.9 ± 3.6 |
| U87MG | 14.8 ± 1.4 | 21.8 ± 1.2 | 27.8 ± 2.2 | 22.9 ± 2.3 |
| HBL100 | 22.8 ± 1.4 | 23.9 ± 1.7 | 22.9 ± 3.8 | 13.9 ± 3.5 |
| HeP2 | 12.9 ± 1.4 | 24.7 ± 2.5 | 19.8 ± 4.8 | 16.4 ± 3.2 |
| L132 | 12.9 ± 2.4 | 18.5 ± 3.6 | 24.7 ± 3.5 | 14.9 ± 4.9 |
| PA-1 | 23.7 ± 3.3 | 32.9 ± 2.6 | 26.7 ± 2.4 | 12.7 ± 3.5 |
| ECV304 | 6.0 ± 2.4 | 20.9 ± 2.3 | 16.5 ± 3.3 | 13.9 ± 4.5 |

SEQ ID NO: 8

Percentage cytotoxicity at different concentrations

| Cell Lines | 1 µM | 100 nM | 10 nM | 1 nM |
|---|---|---|---|---|
| KB | 19.0 ± 4.3 | 23.0 ± 3.2 | 29.0 | 28.0 ± 3.5 |
| U87MG | 21.8 ± 3.4 | 28.9 ± 1.4 | 33.9 ± 2.2 | 23.9 ± 3.3 |
| HBL100 | 25.8 ± 1.4 | 30.6 ± 1.5 | 28.6 ± 3.8 | 9.0 ± 4.5 |
| HeP2 | 12.9 ± 3.4 | 24.9 ± 2.5 | 15.5 ± 4.4 | 12.5 ± 3.2 |
| L132 | 18.6 ± 2.4 | 16.9 ± 3.6 | 27.5 ± 3.5 | 11.9 ± 4.9 |
| PA-1 | 34.4 ± 3.4 | 39.0 ± 2.6 | 26.9 ± 3.4 | 22.1 ± 3.4 |
| ECV304 | 17.9 ± 2.4 | 24.6 ± 2.3 | 31.9 ± 3.3 | 16.9 ± 3.5 |

EXAMPLE 9

In vivo Anti Tumor Activity of Substance P Analogs on PCT Tumor Xenografts Protocol The anti tumor activity of substance P analogs was studied in human colon adenocarcinoma (PTC) xenografts in nude mice. PTC tumor xenografts were grown in Balb/c athymic nude mice by subcutaneous inoculation of a single cell suspension of PTC cells (15×10$^6$ cells/100 µL). The tumor bearing animals were divided into 4 groups of three animals each including one group comprising untreated control animals. Treatment with Substance P Receptor Antagonists was initiated when the average tumor volumes, as measured using a vernier caliper, were between 400–800 mm$^3$. SEQ ID NO:5, SEQ ID NO:7 and SEQ ID NO:8 peptides were prepared at a concentration of 42.5 µg/ml and intravenously administered to the assigned group of tumor bearing animals at a dose of 4.25 µg/100 µL twice a day so that the total dose of 8.5 µg was administered to each animal. The treatment was continued for a period of 10 days.

Results

Figure 1:
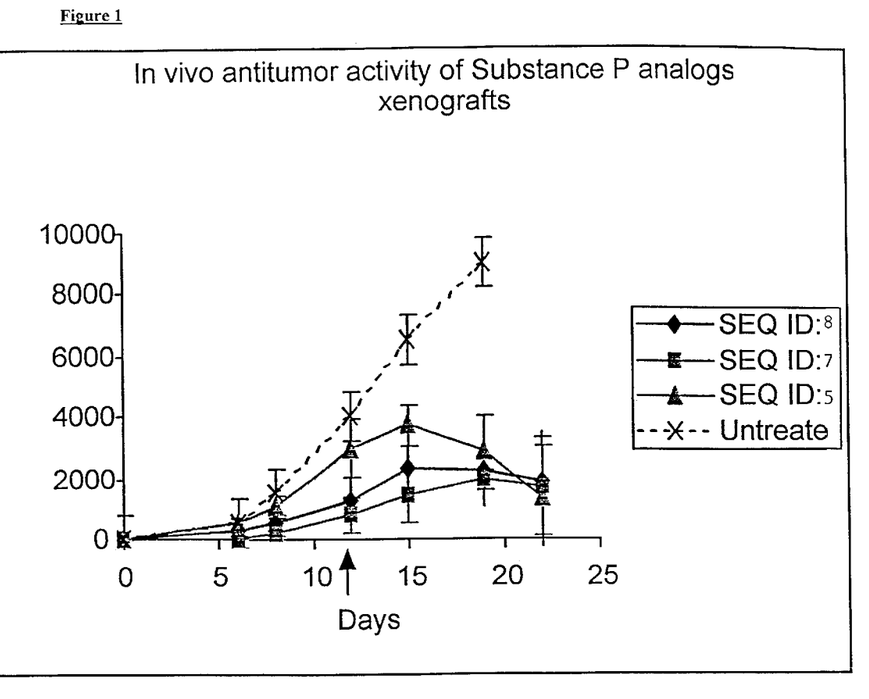
FIG. 1 shows in vivo antitumor activity of substance P analogs on xenografts.

The antitumor activity of the compounds was monitored by measuring 15 tumor volumes every fourth day using the formula W*W*L*0.4 (W=smaller diameter, L=larger diameter). The percentage inhibition of tumor growth was calculated using. the formula (1−tumor volume-treated/ tumor volume-control)×100. Table 4 shows the tumor volumes of individual animals measured till day 21 post-inoculation. FIG. 1 shows the tumor kinetics till day 21 in the treated and untreated animals. All three peptides showed a significant antitumor activity on PTC xenografts. The percentage inhibition of tumor growth caused by SEQ ID NO:5, SEQ ID NO: 7 and SEQ ID NO:8 as compared to controls on day 19 was 68.34%, 78.54% and 75.16% respectively.

TABLE 4

Tumor volumes (mm$^3$) of individual tumor bearing animals of treated and control groups

| | | SEQ ID NO.: 5 | | | | |
|---|---|---|---|---|---|---|
| Day | Untreated | I | II | III | Average | S.D. |
| 0 | 0 | 0 | 0 | 0 | 0 | 0 |
| 6 | 500 | 307.8 | 520 | 687.7 | 505.1 | 190.3 |
| 8 | 1500 | 748.8 | 1149.2 | 1411.2 | 1103.0 | 333.6 |
| 12 | 4000 | 2049 | 3080.3 | 3840.0 | 2989.7 | 898.9 |
| 15 | 6500 | 3310 | 3360 | 4480.0 | 3716.6 | 661.5 |
| 19 | 9000 | 3582 | 1465.6 | 3499.2 | 2848.9 | 1198.7 |
| 22 | — | — | 100 | 2560.0 | 1330.0 | 1739.4 |

| | | SEQ ID NO.: 8 | | | | |
|---|---|---|---|---|---|---|
| Day | Untreated | I | II | III | Average | S.D. |
| 0 | 0 | 0 | 0 | 0 | 0 | 0 |
| 6 | 500 | 532.4 | 291.6 | 0 | 274.6 | 266.6 |
| 8 | 1500 | 1020.6 | 691.2 | 0 | 570.6 | 520.8 |

TABLE 4-continued

Tumor volumes (mm³) of individual tumor bearing animals of treated and control groups

| 12 | 4000 | 2080.8 | 1440 | 156.8 | 1225.8 | 979.7 |
| 15 | 6500 | 3880.8 | 2592 | 580.8 | 2351.2 | 1663.1 |
| 19 | 9000 | 3520.0 | 1474.8 | 1710 | 2234.9 | 1119.0 |
| 22 | — | 2312.0 | 36 | 3177 | 1841.6 | 1622.4 |

SEQ ID NO:: 7

| Day | Untreated | I | II | III | Average | S.D. |
|---|---|---|---|---|---|---|
| 0 | 0 | 0 | 0 | 0 | 0 | 0 |
| 6 | 500 | 25.6 | 66.6 | 0 | 30.7 | 33.5 |
| 8 | 1500 | 176.4 | 260.1 | 72 | 169.5 | 94.2 |
| 12 | 4000 | 580.8 | 1440 | 281.6 | 767.4 | 601.3 |

TABLE 4-continued

Tumor volumes (mm³) of individual tumor bearing animals of treated and control groups

| 15 | 6500 | 946.4 | 2427.6 | 864 | 1412.6 | 879.9 |
| 19 | 9000 | 1741 | 2253 | 1800 | 1931.3 | 280.1 |
| 22 | — | 2018 | 3110 | 0 | 1709.3 | 1577.8 |

All publications referenced are incorporated by reference herein, including the amino acid sequences listed in each publication. All the compounds disclosed and referred to in the publications mentioned above are incorporated by reference herein, including those compounds disclosed and referred to in articles cited by the publications 5 mentioned above.

What is claimed is:

1. A peptide of the formula

X-D-Arg-Pro-Lys-Pro-D-Phe-Gln-D-Trp-Phe-D-Trp-Leu-R-NH$_2$ wherein,

X is acetyl or straight, branched, or cyclic alkanoyl group of from 3 to 18 carbon atoms, or is deleted;

R is Aib (α-aminoisobutyric acid), Deg (α,α-diethylglycine), Dpg (α,α-di-n-propylglycine), Ac5c (1-amino cyclopentane carboxylic acid) or Ac6c (1-aminocyclohexane carboxylic acid) or a hydrolyzable carboxy protecting group; or a pharmaceutically acceptable salt thereof.

2. The peptide of claim 1, wherein X is deleted and R is Ac5c; said peptide having the formula D-Arg-Pro-Lys-Pro-D-Phe-Gln-D-Trp-Phe-D-Trp-Leu-Ac5c-NH$_2$ (SEQ ID NO: 5)

or a pharmaceutically acceptable salt thereof.

3. The peptide of claim 1, wherein X is acetyl and R is Ac5c; said peptide having the formula Acetyl-D-Arg-Pro-Lys-Pro-D-Phe-Gln-D-Trp-Phe-D-Trp-Leu-Ac5c-NH$_2$ (SEQ ID NO: 6)

or a pharmaceutically acceptable salt thereof.

4. The peptide of claim 1, wherein X is butanoyl and R is Ac5c; said peptide having the formula Butanoyl-D-Arg-Pro-Lys-Pro-D-Phe-Gln-D-Trp-Phe-D-Trp-Leu-Ac5c-NH$_2$ (SEQ ID NO: 7)

or a pharmaceutically acceptable salt thereof.

5. The peptide of claim 1, wherein X is octanoyl and R is Ac5c; said peptide having the formula Octanoyl-D-Arg-Pro-Lys-Pro-D-Phe-Gln-D-Trp-Phe-D-Trp-Leu-Ac5c-NH$_2$ (SEQ ID NO: 8)

or a pharmaceutically acceptable salt thereof.

6. The peptide of claim 1, wherein X is lauroyl and R is Ac5c; said peptide having the formula Lauroyl-D-Arg-Pro-Lys-Pro-D-Phe-Gln-D-Trp-Phe-D-Trp-Leu-Ac5c-NH$_2$ (SEQ ID NO: 9)

or a pharmaceutically acceptable salt thereof.

7. The peptide of claim 1, wherein R is Ac6c; said peptide having the formula

D-Arg-Pro-Lys-Pro-D-Phe-Gln-D-Trp-Phe-D-Trp-Leu-Ac6c-NH$_2$ (SEQ ID NO.: 10)

or a pharmaceutically acceptable salt thereof.

8. The peptide of claim 1, wherein X is butanoyl and R is Ac6c; said peptide having the formula Butanoyl-D-Arg-Pro-Lys-Pro-D-Phe-Gln-D-Trp-Phe-D-Trp-Leu-Ac6c-NH$_2$ (SEQ ID NO: 11)

or a pharmaceutically acceptable salt thereof.

9. The peptide of claim 1, wherein x is octanoyl and R is Ac6c; said peptide having the formula Octanoyl-D-Arg-Pro-Lys-Pro-D-Phe-Gln-D-Trp-Phe-D-Trp-Leu-Ac6c-NH$_2$ (SEQ ID NO: 12)

or a pharmaceutically acceptable salt thereof.

10. The peptide of the claim 1, wherein R is Aib; said peptide having the formula D-Arg-Pro-Lys-Pro-D-Phe-Gln-D,-Trp-Phe-D-Trp-Leu-Aib-NH$_2$ (SEQ ID NO: 13)

or a pharmaceutically acceptable salt thereof.

11. The peptide of the claim 1, wherein R is Deg; said peptide having the formula D-Arg-Pro-Lys-Pro-D-Phe-Gln-D-Trp-Phe-D-Trp-Leu-Deg-NH$_2$ (SEQ ID NO: 14)

or a pharmaceutically acceptable salt thereof.

12. The peptide of the claim 1, wherein R is Dpg; said peptide having the formula D-Arg-Pro-Lys-Pro-D-Phe-Gln-D-Trp-Phe-D-Trp-Leu-Dpg-NH$_2$ (SEQ ID NO: 15)

or a pharmaceutically acceptable salt thereof.

13. A composition comprising an effective amount of a polypeptide according to claim 1 and a pharmaceutically acceptable carrier.

14. A method of treatment of cancer in a mammal which comprises administration of an effective amount of a peptide according to claim 1 wherein the cancer is colon cancer.

15. The peptide of the formula

D-Phe-Gln-D-Trp-Phe-D-Trp-Leu-R-NH$_2$ wherein

R is Aib (α-aminoisobutyric acid), Deg (α,α-diethylglycine), Dpg (α,α-di-n-propylglycine), Ac5c (1-amino cyclopentane carboxylic acid) or Ac6c (1-aminocyclohexane carboxylic acid) or a hydrolyzable carboxy protecting group; or a pharmaceutically acceptable salt thereof.

16. The peptide of the claim 15, wherein R is Aib; said peptide having the formula D-Phe-Gln-D-Trp-Phe-D-Trp-Leu-Aib-NH$_2$ (SEQ ID NO: 16)

or a pharmaceutically acceptable salt thereof.

17. The peptide of the claim 15, wherein R is Ac5c; said peptide having the formula D-Phe-Gln-D-Trp-Phe-D-Trp-Leu-Ac5c-NH$_2$ (SEQ ID NO: 17)

or a pharmaceutically acceptable salt thereof.

18. The peptide of claim 15, wherein R is Ac6c; said peptide having the formula

D-Phe-Gln-D-Trp-Phe-D-Trp-Leu-Ac6c-NH$_2$ (SEQ ID NO: 18)

or a pharmaceutically acceptable salt thereof.

19. The peptide of the claim 15, wherein R=Deg; said peptide having the formula

D-Phe-Gln-D-Trp-Phe-D-Trp-Leu-Deg-NH$_2$ (SEQ ID NO: 19)

or a pharmaceutically acceptable salt thereof.

20. The peptide of claim 15, wherein R=Dpg; said peptide having the formula

D-Phe-Gln-D-Trp-Phe-D-Trp-Leu-Dpg-NH$_2$ (SEQ ID NO:20)

or a pharmaceutically acceptable salt thereof.

21. A composition comprising an effective amount of a polypeptide according to claim 15 and a pharmaceutically acceptable carrier.

22. A method of treatment of cancer in a mammal which comprises administration of an effective amount of a peptide according to claim 15 wherein the cancer is colon cancer.

* * * * *

SEQUENCE LISTING

```
<160> NUMBER OF SEQ ID NOS:  20

<210> SEQ ID NO 1
<211> LENGTH: 11
<212> TYPE: PRT
<213> ORGANISM: Equus caballus

<400> SEQUENCE: 1

Arg Pro Lys Pro Gln Gln Phe Phe Gly Leu Met
 1               5                   10

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: This
      peptide was synthetically generated.
<221> NAME/KEY: MOD_RES
<222> LOCATION: (1)
<223> OTHER INFORMATION: /product =pHOPA-D-tryptophan/label =pHOPA-D-
      Trp
<221> NAME/KEY: MOD_RES
<222> LOCATION: (3)
<223> OTHER INFORMATION: /product = D-tryptophan/label = D-Trp

<400> SEQUENCE: 2

Xaa Phe Xaa Leu Leu
 1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: This
      peptide was synthetically generated.
<221> NAME/KEY: MOD_RES
<222> LOCATION: (1)
<223> OTHER INFORMATION: /product = D-methyl-phenylalanine/label = D-
      MePhe
<221> NAME/KEY: MOD_RES
<222> LOCATION: (2)
<223> OTHER INFORMATION: /product = D-tryptophan/label = D-Trp
<221> NAME/KEY: MOD_RES
<222> LOCATION: (4)
<223> OTHER INFORMATION: /product = D-tryptophan/label = D-Trp
<221> NAME/KEY: MOD_RES
```

```
<222> LOCATION: (5)..(6)
<223> OTHER INFORMATION: /product = "OTHER" / note = "surrogate bond
      followed by (CH2NH)"

<400> SEQUENCE: 3

Xaa Xaa Phe Xaa Leu Leu
  1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: This
      peptide was synthetically generated.
<221> NAME/KEY: MOD_RES
<222> LOCATION: (1)
<223> OTHER INFORMATION: /product = D-methylphenylalanine/label = D-
      MePhe
<221> NAME/KEY: MOD_RES
<222> LOCATION: (2)
<223> OTHER INFORMATION: /product = D-tryptophan/label = D-Trp
<221> NAME/KEY: MOD_RES
<222> LOCATION: (4)
<223> OTHER INFORMATION: /product = D-tryptophan/label = D-Trp

<400> SEQUENCE: 4

Xaa Xaa Phe Xaa Leu
  1               5

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: This
      peptide was synthetically generated.
<221> NAME/KEY: MOD_RES
<222> LOCATION: (1)
<223> OTHER INFORMATION: /product = D-arginine/label = D-Arg
<221> NAME/KEY: MOD_RES
<222> LOCATION: (5)
<223> OTHER INFORMATION: /product = D-phenylalanine/label = D-Phe
<221> NAME/KEY: MOD_RES
<222> LOCATION: (7)
<223> OTHER INFORMATION: /product = D-tryptophan/label = D-Trp
<221> NAME/KEY: MOD_RES
<222> LOCATION: (9)
<223> OTHER INFORMATION: /product = D-tryptophan/label = D-Trp
<221> NAME/KEY: MOD_RES
<222> LOCATION: (11)
<223> OTHER INFORMATION: /product = 1-Aminocyclopentane carboxylic
      acid/label = Ac5c

<400> SEQUENCE: 5

Xaa Pro Lys Pro Xaa Gln Xaa Phe Xaa Leu Xaa
  1               5                  10

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: This
      peptide was synthetically generated.
<221> NAME/KEY: MOD_RES
<222> LOCATION: (1)
<223> OTHER INFORMATION: /product = acetyl-D-arginine/label = Acetyl-D-
      Arg
<221> NAME/KEY: MOD_RES
<222> LOCATION: (5)
<223> OTHER INFORMATION: /product = D-phenylalanine/label = D-Phe
<221> NAME/KEY: MOD_RES
```

```
<222> LOCATION: (7)
<223> OTHER INFORMATION: /product = D-tryptophan/label = D-Trp
<221> NAME/KEY: MOD_RES
<222> LOCATION: (9)
<223> OTHER INFORMATION: /product = D-tryptophan/label = D-Trp
<221> NAME/KEY: MOD_RES
<222> LOCATION: (11)
<223> OTHER INFORMATION: /product = 1-Aminocyclopentane carboxylic
      acid/label = Ac5c

<400> SEQUENCE: 6

Xaa Pro Lys Pro Xaa Gln Xaa Phe Xaa Leu Xaa
 1               5                   10

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: This
      peptide was synthetically generated.
<221> NAME/KEY: MOD_RES
<222> LOCATION: (1)
<223> OTHER INFORMATION: /product = Butanoyl- D-arginine/label =Butanoyl
      - D-Arg
<221> NAME/KEY: MOD_RES
<222> LOCATION: (5)
<223> OTHER INFORMATION: /product = D-phenylalanine/label = D-Phe
<221> NAME/KEY: MOD_RES
<222> LOCATION: (7)
<223> OTHER INFORMATION: /product = D-tryptophan/label = D-Trp
<221> NAME/KEY: MOD_RES
<222> LOCATION: (9)
<223> OTHER INFORMATION: /product = D-tryptophan/label = D-Trp
<221> NAME/KEY: MOD_RES
<222> LOCATION: (11)
<223> OTHER INFORMATION: /product = 1-Aminocyclopentane carboxylic
      acid/label = Ac5c

<400> SEQUENCE: 7

Xaa Pro Lys Pro Xaa Gln Xaa Phe Xaa Leu Xaa
 1               5                   10

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: This
      peptide was synthetically generated.
<221> NAME/KEY: MOD_RES
<222> LOCATION: (1)
<223> OTHER INFORMATION: /product = Octanoyl- D-arginine/label =
      Octanoyl-D-Arg
<221> NAME/KEY: MOD_RES
<222> LOCATION: (5)
<223> OTHER INFORMATION: /product = D-phenylalanine/label = D-Phe
<221> NAME/KEY: MOD_RES
<222> LOCATION: (7)
<223> OTHER INFORMATION: /product = D-tryptophan/label = D-Trp
<221> NAME/KEY: MOD_RES
<222> LOCATION: (9)
<223> OTHER INFORMATION: /product = D-tryptophan/label = D-Trp
<221> NAME/KEY: MOD_RES
<222> LOCATION: (11)
<223> OTHER INFORMATION: /product = 1-Aminocyclopentane carboxylic
      acid/label = Ac5c

<400> SEQUENCE: 8

Xaa Pro Lys Pro Xaa Gln Xaa Phe Xaa Leu Xaa
 1               5                   10

<210> SEQ ID NO 9
```

```
<211> LENGTH: 11
<212> TYPE: PRT
<213> ORGANISM: Artificial Sequence
<220> FEATURE:
<223> OTHER INFORMATION: Description of Artificial Sequence: This
      peptide was synthetically generated.
<221> NAME/KEY: MOD_RES
<222> LOCATION: (1)
<223> OTHER INFORMATION: /product = Lauroyl-D-arginine/label = Lauroyl
      D-Arg
<221> NAME/KEY: MOD_RES
<222> LOCATION: (5)
<223> OTHER INFORMATION: /product = D-phenylalanine/label = D-Phe
<221> NAME/KEY: MOD_RES
<222> LOCATION: (7)
<223> OTHER INFORMATION: /product = D-tryptophan/label = D-Trp
<221> NAME/KEY: MOD_RES
<222> LOCATION: (9)
<223> OTHER INFORMATION: /product = D-tryptophan/label = D-Trp
<221> NAME/KEY: MOD_RES
<222> LOCATION: (11)
<223> OTHER INFORMATION: /product = 1-Aminocyclopentane carboxylic
      acid/label = Ac5c

<400> SEQUENCE: 9

Xaa Pro Lys Pro Xaa Gln Xaa Phe Xaa Leu Xaa
  1               5                  10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: This
      peptide was synthetically generated.
<221> NAME/KEY: MOD_RES
<222> LOCATION: (1)
<223> OTHER INFORMATION: /product = D-arginine/label = D-Arg
<221> NAME/KEY: MOD_RES
<222> LOCATION: (5)
<223> OTHER INFORMATION: /product = D-phenylalanine/label = D-Phe
<221> NAME/KEY: MOD_RES
<222> LOCATION: (7)
<223> OTHER INFORMATION: /product = D-tryptophan/label = D-Trp
<221> NAME/KEY: MOD_RES
<222> LOCATION: (9)
<223> OTHER INFORMATION: /product = D-tryptophan/label = D-Trp
<221> NAME/KEY: MOD_RES
<222> LOCATION: (11)
<223> OTHER INFORMATION: /product = 1-Aminocyclohexane carboxylic
      acid/label = Ac6c

<400> SEQUENCE: 10

Xaa Pro Lys Pro Xaa Gln Xaa Phe Xaa Leu Xaa
  1               5                  10

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: This
      peptide was synthetically generated.
<221> NAME/KEY: MOD_RES
<222> LOCATION: (1)
<223> OTHER INFORMATION: /product = Butanoyl-D-arginine/label =
      Butanoyl-D-Arg
<221> NAME/KEY: MOD_RES
<222> LOCATION: (5)
<223> OTHER INFORMATION: /product = D-phenylalanine/label = D-Phe
<221> NAME/KEY: MOD_RES
<222> LOCATION: (7)
<223> OTHER INFORMATION: /product = D-tryptophan/label = D-Trp
<221> NAME/KEY: MOD_RES
<222> LOCATION: (9)
```

```
<223> OTHER INFORMATION: /product = D-tryptophan/label = D-Trp
<221> NAME/KEY: MOD_RES
<222> LOCATION: (11)
<223> OTHER INFORMATION: 1-Aminocyclohexane carboxylic acid/label =
      Ac6c

<400> SEQUENCE: 11

Xaa Pro Lys Pro Xaa Gln Xaa Phe Xaa Leu Xaa
 1               5                   10

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: This
      peptide was synthetically generated.
<221> NAME/KEY: MOD_RES
<222> LOCATION: (1)
<223> OTHER INFORMATION: /product = Octanoyl-D-arginine/label =
      Octanoyl-D-Arg
<221> NAME/KEY: MOD_RES
<222> LOCATION: (5)
<223> OTHER INFORMATION: /product = D-phenylalanine/label = D-Phe
<221> NAME/KEY: MOD_RES
<222> LOCATION: (7)
<223> OTHER INFORMATION: /product = D-tryptophan/label = D-Trp
<221> NAME/KEY: MOD_RES
<222> LOCATION: (9)
<223> OTHER INFORMATION: /product = D-tryptophan/label = D-Trp
<221> NAME/KEY: MOD_RES
<222> LOCATION: (11)
<223> OTHER INFORMATION: /product = 1-Aminocyclohexane carboxylic
      acid/label = Ac6c

<400> SEQUENCE: 12

Xaa Pro Lys Pro Xaa Gln Xaa Phe Xaa Leu Xaa
 1               5                   10

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence:  This
      peptide was synthetically generated.
<221> NAME/KEY: MOD_RES
<222> LOCATION: (1)
<223> OTHER INFORMATION: /product = D-arginine/label = D-Arg
<221> NAME/KEY: MOD_RES
<222> LOCATION: (5)
<223> OTHER INFORMATION: /product = D-phenylalanine/label = D-Phe
<221> NAME/KEY: MOD_RES
<222> LOCATION: (7)
<223> OTHER INFORMATION: /product = D-tryptophan/label = D-Trp
<221> NAME/KEY: MOD_RES
<222> LOCATION: (9)
<223> OTHER INFORMATION: /product = D-tryptophan/label = D-Trp
<221> NAME/KEY: MOD_RES
<222> LOCATION: (11)
<223> OTHER INFORMATION: /product = alpha-aminoisobutyric acid/label =
      Aib

<400> SEQUENCE: 13

Xaa Pro Lys Pro Xaa Gln Xaa Phe Xaa Leu Xaa
 1               5                   10

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: This
``` peptide was synthetically generated.
<221> NAME/KEY: MOD_RES
<222> LOCATION: (1)
<223> OTHER INFORMATION: /product = D-arginine/label = D-Arg
<221> NAME/KEY: MOD_RES
<222> LOCATION: (5)
<223> OTHER INFORMATION: /product = D-phenylalanine/label = D-Phe
<221> NAME/KEY: MOD_RES
<222> LOCATION: (7)
<223> OTHER INFORMATION: /product = D-tryptophan/label = D-Trp
<221> NAME/KEY: MOD_RES
<222> LOCATION: (9)
<223> OTHER INFORMATION: /product = D-tryptophan/label = D-Trp
<221> NAME/KEY: MOD_RES
<222> LOCATION: (11)
<223> OTHER INFORMATION: /product = alpha,alpha-di-ethyl glycine/
      label = Deg

<400> SEQUENCE: 14

Xaa Pro Lys Pro Xaa Gln Xaa Phe Xaa Leu Xaa
 1               5                   10

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: This
      peptide was synthetically generated.
<221> NAME/KEY: MOD_RES
<222> LOCATION: (1)
<223> OTHER INFORMATION: /product = D-arginine/label = D-Arg
<221> NAME/KEY: MOD_RES
<222> LOCATION: (5)
<223> OTHER INFORMATION: /product = D-phenylalanine/label = D-Phe
<221> NAME/KEY: MOD_RES
<222> LOCATION: (7)
<223> OTHER INFORMATION: /product = D-tryptophan/label = D-Trp
<221> NAME/KEY: MOD_RES
<222> LOCATION: (9)
<223> OTHER INFORMATION: /product = D-tryptophan/label = D-Trp
<221> NAME/KEY: MOD_RES
<222> LOCATION: (11)
<223> OTHER INFORMATION: /product = alpha,alpha-di-n-propylglycine/
      label = Dpg

<400> SEQUENCE: 15

Xaa Pro Lys Pro Xaa Gln Xaa Phe Xaa Leu Xaa
 1               5                   10

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: This
      peptide was synthetically generated.
<221> NAME/KEY: MOD_RES
<222> LOCATION: (1)
<223> OTHER INFORMATION: /product = D-phenylalanine/label = D-Phe
<221> NAME/KEY: MOD_RES
<222> LOCATION: (3)
<223> OTHER INFORMATION: /product = D-tryptophan/label = D-Trp
<221> NAME/KEY: MOD_RES
<222> LOCATION: (5)
<223> OTHER INFORMATION: /product = D-tryptophan/label = D-Trp
<221> NAME/KEY: MOD_RES
<222> LOCATION: (7)
<223> OTHER INFORMATION: /product = alpha-aminoisobutyric acid/label =
      Aib

<400> SEQUENCE: 16

Xaa Gln Xaa Phe Xaa Leu Xaa
 1               5

```
<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: This
      peptide was synthetically generated.
<221> NAME/KEY: MOD_RES
<222> LOCATION: (1)
<223> OTHER INFORMATION: /product = D-phenylalanine/label = D-Phe
<221> NAME/KEY: MOD_RES
<222> LOCATION: (3)
<223> OTHER INFORMATION: /product = D-tryptophan/label = D-Trp
<221> NAME/KEY: MOD_RES
<222> LOCATION: (5)
<223> OTHER INFORMATION: /product = D-tryptophan/label = D-Trp
<221> NAME/KEY: MOD_RES
<222> LOCATION: (7)
<223> OTHER INFORMATION: /product = 1-Aminocyclopentane carboxylic
      acid/label = Ac5c

<400> SEQUENCE: 17

Xaa Gln Xaa Phe Xaa Leu Xaa
 1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: This
      peptide was synthetically generated.
<221> NAME/KEY: MOD_RES
<222> LOCATION: (1)
<223> OTHER INFORMATION: /product = D-phenylalanine/label = D-Phe
<221> NAME/KEY: MOD_RES
<222> LOCATION: (3)
<223> OTHER INFORMATION: /product = D-tryptophan/label = D-Trp
<221> NAME/KEY: MOD_RES
<222> LOCATION: (5)
<223> OTHER INFORMATION: /product = D-tryptophan/label = D-Trp
<221> NAME/KEY: MOD_RES
<222> LOCATION: (7)
<223> OTHER INFORMATION: /product = 1-aminocyclohexane carboxylic
      acid/label = Ac6c

<400> SEQUENCE: 18

Xaa Gln Xaa Phe Xaa Leu Xaa
 1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: This
      peptide was synthetically generated.
<221> NAME/KEY: MOD_RES
<222> LOCATION: (1)
<223> OTHER INFORMATION: /product = D-phenylalanine/label = D-Phe
<221> NAME/KEY: MOD_RES
<222> LOCATION: (3)
<223> OTHER INFORMATION: /product = D-tryptophan/label = D-Trp
<221> NAME/KEY: MOD_RES
<222> LOCATION: (5)
<223> OTHER INFORMATION: /product = D-tryptophan/label = D-Trp
<221> NAME/KEY: MOD_RES
<222> LOCATION: (7)
<223> OTHER INFORMATION: /product = alpha,alpha-Di-ethyl glycine/
      label = Deg

<400> SEQUENCE: 19
```

```
Xaa Gln Xaa Phe Xaa Leu Xaa
 1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: This
      peptide was synthetically generated.
<221> NAME/KEY: MOD_RES
<222> LOCATION: (1)
<223> OTHER INFORMATION: /product = D-phenylalanine/label = D-Phe
<221> NAME/KEY: MOD_RES
<222> LOCATION: (3)
<223> OTHER INFORMATION: /product = D-tryptophan/label = D-Trp
<221> NAME/KEY: MOD_RES
<222> LOCATION: (5)
<223> OTHER INFORMATION: /product = D-tryptophan/label = D-Trp
<221> NAME/KEY: MOD_RES
<222> LOCATION: (7)
<223> OTHER INFORMATION: /product = alpha,alpha-di-n-propylglycine/
      label = Dpg

<400> SEQUENCE: 20

Xaa Gln Xaa Phe Xaa Leu Xaa
 1               5
```